United States Patent [19]

Barth et al.

[11] Patent Number: 5,462,960
[45] Date of Patent: Oct. 31, 1995

[54] PYRAZOLE-3-CARBOXAMIDE DERIVATIVES, PROCESS FOR THEIR PREPARATION AND PHARMACEUTICAL COMPOSITIONS IN WHICH THEY ARE PRESENT

[75] Inventors: Francis Barth; Pierre Casellas, both of Montpellier; Christian Congy, Saint Gely du Fesc; Serge Martinez, Montpellier; Murielle Rinaldi, Saint Georges d'Orques, all of France

[73] Assignee: Sanofi, Paris, France

[21] Appl. No.: 357,880

[22] Filed: Dec. 16, 1994

[30] Foreign Application Priority Data

Dec. 17, 1993 [FR] France .................. 93 15221

[51] Int. Cl.$^6$ .................. C07D 231/14; A61K 31/415
[52] U.S. Cl. .................. 514/406; 548/374.1; 514/341; 546/16; 546/279; 546/97
[58] Field of Search .................. 548/374.1; 546/279, 546/16, 97; 514/406, 341

[56] References Cited

U.S. PATENT DOCUMENTS 3,449,350  6/1969  Walker .................. 260/295.5
5,013,837  5/1991  Ward et al. .................. 544/143

FOREIGN PATENT DOCUMENTS 0445781   9/1991  European Pat. Off. .
0477049   3/1992  European Pat. Off. .
0576357  12/1993  European Pat. Off. .

OTHER PUBLICATIONS

Mustafa, A., et al., "Behavior of the Hetero-Ring in γ-Phenyl-Δ$^{βγ}$-Butenolide Derivatives Toward Hydrizines, Acid Rearrangement of 4-Phenylazo-2-Phenyloxazolin-5-One", *Can. J. Chem.,* vol. 41 (1963), p. 1813 et seq.

Khattab, S., et al., "Structure of the Diazonium Coupling Product of γ-Phenyl-Δ$^{βγ}$-Butenolide", *J. Chem. & Engr. Data,* vol. 22 (1977), p. 104 et seq.

*Primary Examiner*—Johann Richter
*Assistant Examiner*—Laura Cross
*Attorney, Agent, or Firm*—Bacon & Thomas

[57] ABSTRACT

The present invention relates to novel pyrazole-3-carboxamide derivatives of the formula

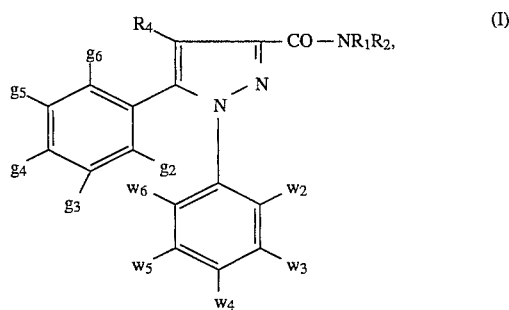

in which the substituents are as defined in the specification.

The present invention further relates to a process for the preparation of these novel derivatives and to the pharmaceutical compositions in which they are present.

20 Claims, No Drawings

PYRAZOLE-3-CARBOXAMIDE DERIVATIVES, PROCESS FOR THEIR PREPARATION AND PHARMACEUTICAL COMPOSITIONS IN WHICH THEY ARE PRESENT

The present invention relates to novel pyrazole-3-carboxamide derivatives and their salts, to a process for their preparation and to pharmaceutical compositions in which they are present.

Numerous pyrazole derivatives have been described in the literature; more particularly, EP-A-268554 and DE-A-3910248 claim pyrazoles possessing herbicidal properties, EP-A-430186 and JP-A-3 031840 claim compounds useful for photography, and EP-A-418845 claims pyrazoles possessing antiinflammatory, analgesic and antithrombotic activity.

It has now been found that the pyrazole-3-carboxamide derivatives forming the subject of the invention possess a very good affinity for the cannabinoid receptor and are useful in the therapeutic areas in which cannabis is known to be involved.

$\Delta^9$-THC ($\Delta^9$-tetrahydrocannabinol) is the principal active constituent extracted from *Cannabis sativa* (Tuner, 1985; In Marijuana 84, Ed. Harvey, DY, IRL Press, Oxford).

The effects of cannabinoids are due to an interaction with high-affinity specific receptors present in the central nervous system (Devane et al., Molecular Pharmacology, 1988, 34, 605–613) and in the peripheral nervous system (Nye et al., J. Pharmacol. Exp. Ther., 1985, 234, 784–791; Kaminski et al., Molecular Pharmacology, 1992, 42, 736–742; Munro et al., Nature, 1993, 365, 61–65; Bouaboula et al., Eur. J. Biochem., 1993, 214, 173–180).

The therapeutic indications of cannabinoids concern a variety of areas such as the immune system, the central nervous system and the cardiovascular or endocrine system (Hollister, Pharmacological Reviews, 1986, 38, 1–20, Renv and Sinha, Progress in Drug Research, 1991, 36, 71–114, and Consroe and Sandyk, in Marijuana/Cannabinoids, Neurobiology and Neurophysiology, p. 459, Eds L. Murphy and A. Barthe, CRC Press, 1992).

The characterization of this receptor has been made possible by the development of specific synthetic ligands such as the agonists WIN 55212-2 (J. Pharmacol. Exp. Ther., 1993, 264, 1352–1363) or CP 55,940 (J. Pharmacol. Exp. Ther., 1988, 247, 1046–1051).

According to one of its features, the present invention relates to the compounds of the formula

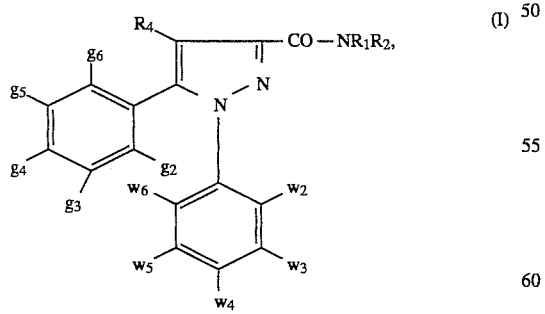

in which:

$g_2$, $g_3$, $g_4$, $g_5$ and $g_6$, and $w_2$, $w_3$, $w_4$, $w_5$ and $w_6$, are identical or different and are independently hydrogen, a chlorine, bromine or iodine atom, a ($C_1$–$C_3$)alkyl, a ($C_1$–$C_3$)alkoxy, a trifluoromethyl or a nitro group and $g_4$ can also be a phenyl group;

$R_1$ is a ($C_1$–$C_6$)alkyl or a hydrogen;
$R_2$ is -$^+NR_3R_5R_6$ or —$NR_5R_6$;
$R_3$ is a ($C_1$–$C_6$)alkyl or $R_3$ forms a bridge with one of the atoms of the heterocyclic radical formed by $NR_5R_6$;
$R_4$ is hydrogen or a ($C_1$–$C_5$)alkyl; and
$R_5$ is hydrogen or a ($C_1$–$C_6$)alkyl and $R_6$ is hydrogen, a ($C_1$–$C_6$)alkyl, a phenyl or a ($C_3$–$C_8$)cycloalkyl, or $R_5$ and $R_6$, together with the nitrogen atom to which they are bonded, form a 5- to 10-membered saturated or unsaturated heterocyclic radical which is unsubstituted or monosubstituted or polysubstituted by a ($C_1$–$C_6$)alkyl, a benzyl, a phenyl, a hydroxyl, a ($C_1$–$C_6$)alkoxy or a halogen, with the proviso that if $R_2$ is $NR_5R_6$, $R_5$ and $R_6$, together with the nitrogen atom to which they are bonded, form a heterocyclic radical other than a 5- to 8-membered saturated radical which is unsubstituted or substituted by a ($C_1$–$C_3$)alkyl, a hydroxyl or a benzyl, their salts or their solvates.

($C_1$–$C_3$)alkyl, ($C_1$–$C_5$)alkyl and ($C_1$–$C_6$)alkyl are understood as meaning $C_1$–$C_3$, $C_1$–$C_5$ and $C_1$–$C_6$ linear or branched alkyls. The preferred alkyl groups are methyl, ethyl, propyl and isopropyl groups.

5- or 10-membered saturated or unsaturated heterocyclic radical is understood as meaning a fused or bridged, mono-, di- or tri-cyclic, non-aromatic heterocyclic radical which can contain a second heteroatom such as nitrogen, oxygen or sulfur. These radicals include the following radicals in particular: pyrrolidin-1-yl, piperidin-1-yl, hexahydroazepin-1-yl, morpholin-4-yl, thiomorpholin-4-yl, 2-azabicyclo[2.2.2]oct-5-en-2-yl, 2-methyl-2-azoniabicyclo[2.2.2]oct-5-en-2-yl, 2-azaadamant-2-yl, 1,2,3,6-tetrahydropyridin-1-yl, 2-azabicyclo[2.2.1]heptan-2-yl, 2-azabicyclo[2.2.2]octan-2-yl and 1-azoniabicyclo[2.2.2]octan-1-yl.

The salts of the compound of formula (I) include the pharmaceutically acceptable acid addition salts such as the hydrochloride, hydrobromide, sulfate, hydrogensulfate, dihydrogenphosphate, methanesulfonate, methylsulfate, maleate, oxalate, fumarate, naphthalene-2-sulfonate, glyconate, gluconate, citrate, isethionate, paratoluenesulfonate and mesitylenesulfonate.

Advantageously, the present invention relates to compounds of the formula

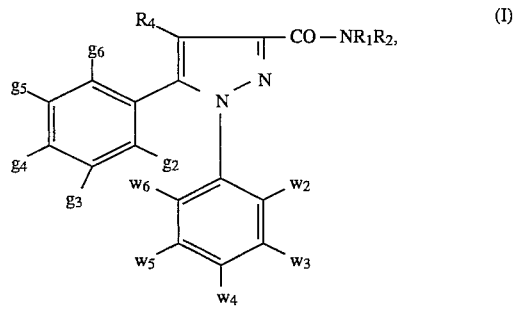

in which:

$g_2$, $g_3$, $g_4$, $g_5$ and $g_6$, and $w_2$, $w_3$, $w_4$, $w_5$ and $w_6$, are identical or different and are independently hydrogen, a chlorine, bromine or iodine atom, a ($C_1$–$C_3$)alkyl, a ($C_1$–$C_3$)alkoxy, a trifluoromethyl or a nitro group and $g_4$ can also be a phenyl group;

$R_1$ is a hydrogen or a ($C_1$–$C_6$)alkyl;
$R_2$ is -$^+NR_3R_5R_6$ or —$NR_5R_6$;
$R_3$ is a ($C_1$–$C_6$)alkyl or $R_3$ forms a bridge with one of the atoms of the heterocyclic radical formed by $NR_5R_6$;
$R_4$ is hydrogen or a ($C_1$–$C_5$)alkyl; and
$R_5$ and $R_6$, together with the nitrogen atom to which they are bonded, form a 5- to 10-membered saturated or unsaturated heterocyclic radical which is unsubstituted or monosubstituted or polysubstituted by a ($C_1$–$C_6$)alkyl, a benzyl, a phenyl, a hydroxyl, a ($C_1$–$C_6$)alkoxy or a halogen, with the proviso that if $R_2$ is $NR_5R_6$, $R_5$ and $R_6$, together with the nitrogen atom to which they are bonded, form a heterocyclic radical other than a 5- to 8-membered saturated radical which is unsubstituted or substituted by a ($C_1$–$C_3$)alkyl, a hydroxyl or a benzyl, their salts or their solvates.

In formula (I) above, preferably at least one of the substituents $w_2$, $w_3$, $w_4$, $w_5$, $w_6$, $g_2$, $g_3$, $g_4$, $g_5$ and $g_6$ is other than hydrogen.

The compounds (I) in which at least one of the substituents $w_2$, $w_3$, $w_4$, $w_5$, $w_6$, $g_2$, $g_3$, $g_4$, $g_5$ and $g_6$ is selected from a chlorine and a methyl are preferred.

Particularly preferred compounds are those in which $w_2$, $w_4$ and $g_4$ are chlorine atoms.

The compounds (I) in which $R_4$ is H, methyl or ethyl are preferred.

The preferred compounds of formula (I) are those in which $w_2$, $w_4$ and $g_4$ are each a chlorine, $R_1$ is hydrogen, $R_4$ is a methyl or an ethyl and $R_2$ has one of the meanings indicated above for (I).

Other preferred compounds (I) according to the invention are those in which $g_4$ is a chlorine or a methyl, $w_3$ and $w_4$, or $w_2$ and $w_5$, are selected from chlorine and methyl, $R_1$ is a methyl, an ethyl or a propyl, $R_4$ is hydrogen and $R_2$ has one of the meanings indicated above for (I).

The compounds (I) in which $R_2$ is a 5-, 6- or 7-membered monounsaturated heterocyclic radical are preferred.

More particularly preferred compounds (I) are those in which $R_2$ is a 1,2,3,6-tetrahydropyridin-1-yl group.

According to another of its features, the present invention relates to a process for the preparation of a compound (I), its salts and their solvates, which comprises treating a functional derivative of the pyrazole-3-carboxylic acid of the formula

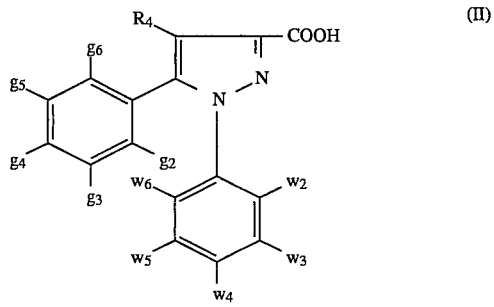

(II)

in which $w_2$, $w_3$, $w_4$, $w_5$, $w_6$, $g_2$, $g_3$, $g_4$, $g_5$, $g_6$ and $R_4$ are as defined for (I), with an amine of the formula $HNR_1R_2$, in which $R_1$ and $R_2$ are as defined for (I), and optionally converting the resulting compound to one of its salts or their solvates.

The functional derivative of the acid (II) which can be used is the acid chloride, the anhydride, a mixed anhydride, a ($C_1$–$C_4$)alkyl ester, in which the alkyl is linear or branched, an activated ester, for example the p-nitrophenyl ester, or the free acid appropriately activated for example with N,N-dicyclohexylcarbodiimide or with benzotriazole-N-oxotris-(dimethylamino)phosphonium hexafluorophosphate (BOP).

Thus, in the process according to the invention, the pyrazole-3-carboxylic acid chloride, obtained by reacting thionyl chloride with the acid of formula (II), can be reacted with an amine $HNR_1R_2$ in a solvent such as dichloromethane, under an inert atmosphere, at a temperature of between 0° C. and room temperature, in the presence of a base such as triethylamine.

One variant of the procedure consists in preparing the mixed anhydride of the acid of formula (II) by reacting ethyl chloroformate with the acid of formula (II) in the presence of a base such as triethylamine, and in reacting said mixed anhydride with an amine $HNR_1R_2$ in a solvent such as dichloromethane, under an inert atmosphere, at room temperature, in the presence of a base such as triethylamine.

The compound of formula (I) obtained in this way is isolated in the form of the free base or a salt or solvate by the conventional techniques.

If the compound of formula (I) is isolated in the form of one of its salts, for example the hydrochloride or oxalate, the free base can be prepared by neutralization of said salt with a mineral or organic base such as sodium or ammonium hydroxide, triethylamine or an alkali metal carbonate or bicarbonate like sodium or potassium carbonate or bicarbonate, and converted to another salt such as the methanesulfonate, fumarate or naphthalene-2-sulfonate.

If the compound (I) is obtained in the form of the free base, salification is effected by treatment with the chosen acid in an organic solvent. Treatment of the free base, dissolved for example in an ether such as diethyl ether or in acetone, with a solution of the acid in the same solvent gives the corresponding salt, which is isolated by the conventional techniques.

The compounds of formula (I) in which $R_2$ is $-^+NR_3R_5R_6$ and $R_3$ is a ($C_1$–$C_6$)alkyl are preferably obtained by reacting an alkyl halide ($R_3$Hal), in which the alkyl is $C_1$–$C_6$ and the halogen is selected from bromine or iodine, with a compound of formula (I) in which $R_2$ is —$NR_5R_6$.

The compounds of formula (I) in which $R_2$ is $-^+NR_3R_5R_6$ and $R_3$ forms a bridge with one of the atoms of the heterocyclic radical formed by $NR_5R_6$ are obtained by reacting a compound of the formula $$NH_2—N^+R_3R_5R_6$$

with a functional derivative of the pyrazole-3-carboxylic acid of formula (II).

The acid of formula (II) used as the starting compound for the process of the present invention can be prepared by conventional methods.

In a preferred procedure, the derivatives of the pyrazole-3-carboxylic acid of formula (II) can be synthesized from the corresponding esters.

If $R_4$ is H or a methyl group, said esters are synthesized by applying the method described in Berichte, 1887, 20, 2185; they make it possible to prepare the esters in which $R_4$ is a ($C_2$–$C_5$)alkyl.

The reaction scheme for the preparation of the compounds (II) via their methyl or ethyl ester (Alk=$CH_3$ or $C_2H_5$) is represented by SCHEME 1 below.

SCHEME 1

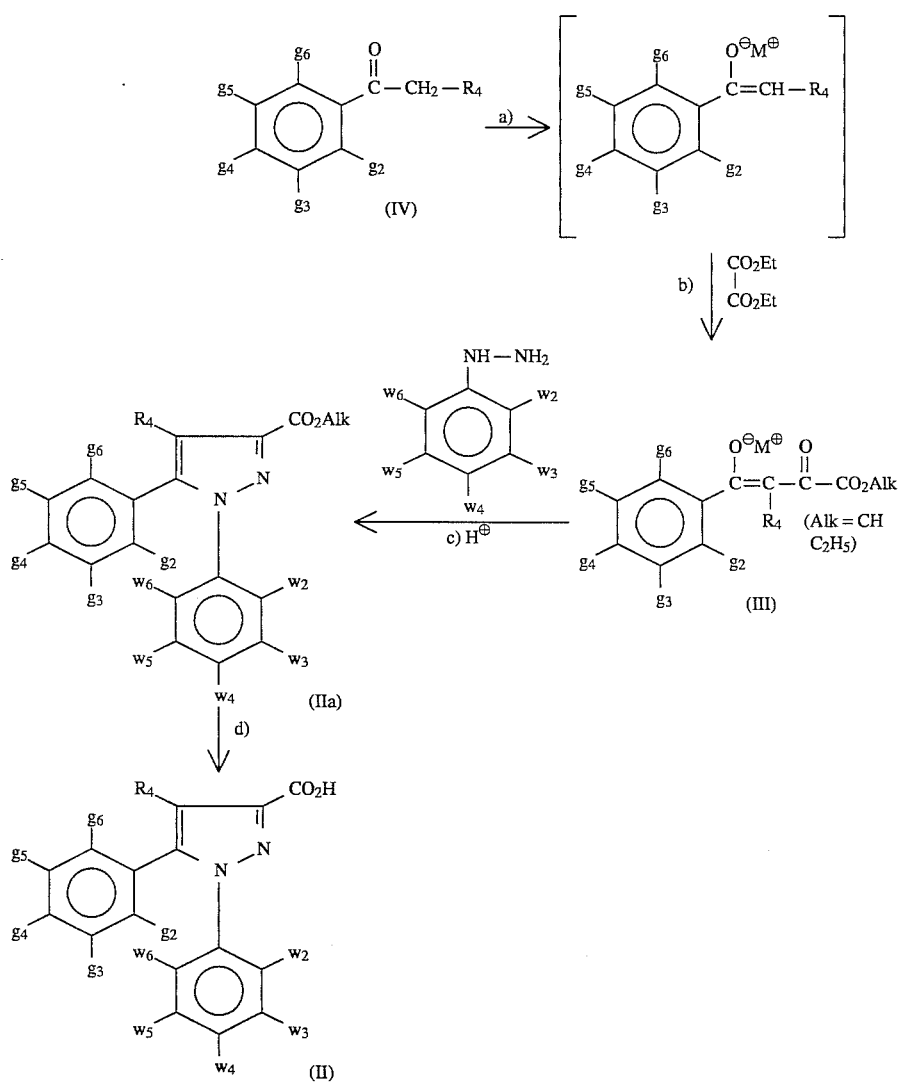

The first step, a), consists in preparing an alkali metal salt of an acetophenone derivative of formula (IV), in which $R_4$, $g_2$, $g_3$, $g_4$, $g_5$ and $g_6$ are as defined above for (I), to which an equimolar amount of diethyl oxalate is then added (step b) to give the ketoester of formula (III).

In the case where $R_4$=H, the alkali metal will preferably be sodium and the ketoester salt (III) (Alk=CH$_3$) will be obtained by the procedure described in Bull. Soc. Chim. Fr., 1947, 14, 1098, using sodium methylate in methanol to perform step a).

In the case where $R_4$=CH$_3$, the alkali metal will preferably be lithium and the ketoester salt (III) (Alk=C$_2$H$_5$) will be obtained according to J. Heterocyclic Chem., 1989, 26, 1389, using the lithium salt of hexamethyldisilazane in ethyl ether to perform step a).

The alkali metal salts (III) prepared in this way are then refluxed in acetic acid with excess hydrazine derivative (step c). Precipitation in iced water gives the pyrazole-3-carboxylic acid esters (IIa).

These esters (IIa) are then converted to their acids (II) by reaction with an alkaline agent such as, for example, potassium hydroxide, followed by acidification (step d).

Preferably, if $R_4$ is a (C$_2$–C$_5$)alkyl, the process described in SCHEME 2 below is used to prepare the pyrazole-3-carboxylic acids of formula (II).

SCHEME 2

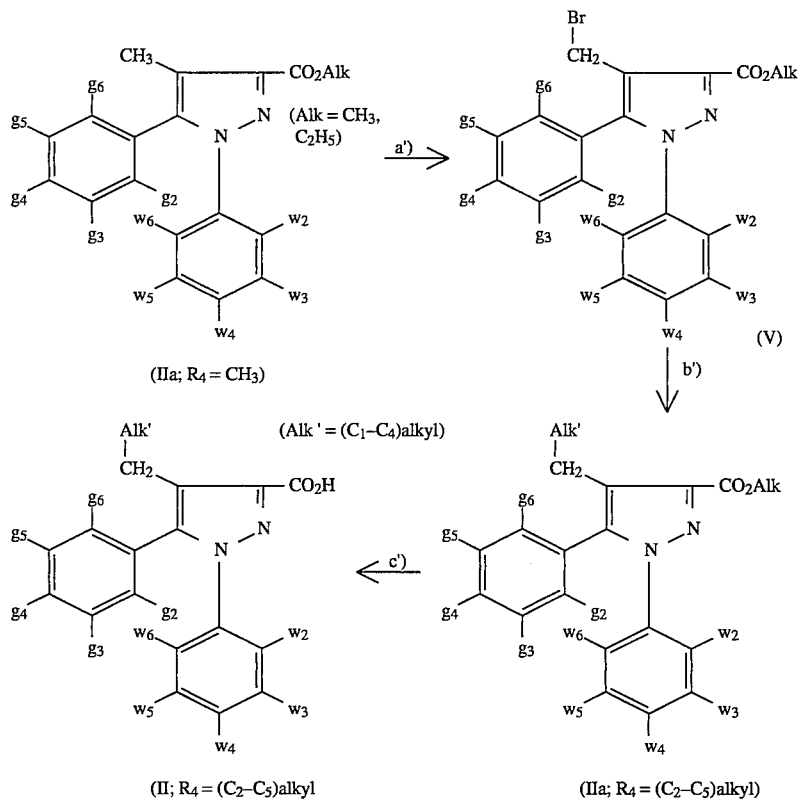

(IIa; $R_4 = CH_3$)

(V)

(II; $R_4 = (C_2-C_5)$alkyl)

(IIa; $R_4 = (C_2-C_5)$alkyl)

The first step, a'), consists in preparing a 4-bromomethylpyrazole of formula (V) by reacting N-bromosuccinimide with an ester (IIa) in which $R_4$ is a $CH_3$. The reaction takes place in a solvent such as carbon tetrachloride, in the presence of dibenzoyl peroxide.

Step b') consists in preparing an ester (IIa) in which $R_4$ is a $(C_2-C_5)$alkyl by reaction with an organocuprate $(Alk')_2CuLi$, in which Alk' is a $(C_1-C_4)$alkyl, in a solvent such as diethyl ether, at a temperature below or equal to $-20°$C.

This ester (IIa) is then converted to its acid (II) by reaction with an alkaline agent such as, for example, potassium hydroxide, followed by acidification (step c').

The amines $HNR_1R_2$ are known or are prepared by known methods.

More particularly, the amines $HNR_1NR_5R_6$ in which $R_1=H$ can be obtained by the process described in Chem. Ber., 1986, 119, 1413–1423, which consists in reducing a nitroso derivative of the formula

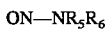   (VI)

in which $R_5$ and $R_6$ are as defined above for (I), with a hydride such as lithium aluminum hydride. The nitroso derivative (VI) is obtained by reacting a compound of the formula

   (VII)

in which $R_5$ and $R_6$ are as defined above for (I), with sodium nitrite in aqueous solution, in the presence of an acid such as acetic acid.

The compounds of formula (VII) are known or are prepared by known methods.

More particularly, the amines $HNR_1NR_5R_6$ in which $R_1=CH_3$ can be obtained by the process described by Zinner et al., Arch. Pharm. (Weinheim, Ger.), 1966, 299, 245–248, and the amines $HNR_1NR_5R_6$ in which $R_1=(C_2-C_6)$alkyl can be obtained by the process described in patent DE 24 09 431 from the amines $HNR_1NR_5R_6$ in which $R_1=H$.

2-Amino-2-azabicyclo[2.2.2]oct-5-ene is prepared according to Chem. Ber., 1986, 119, 1413–1423.

2-Amino-2-methyl-2-azoniabicyclo[2.2.2]oct-5-ene chloride is prepared according to Chem. Ber., 1989, 122, 1153.

2-Amino-2-azaadamantane is prepared from 2-azaadamantane via the nitroso derivative. 2-Azaadamantane is prepared according to J. Org. Chem., 1981, 46, 4953.

1-Amino-1-azoniabicyclo[2.2.2]octane mesitylenesulfonate is prepared according to J. Heterocyclic Chem., 1980, 17, 1241.

The compounds of formula (I) possess a very good affinity in vitro for the central and/or peripheral cannabinoid receptors under the experimental conditions described by Devane et al., Molecular Pharmacology, 1988, 34, 605–613.

The compounds according to the invention also possess an affinity for the cannabinoid receptors present on preparations of electrically stimulated isolated organs. These tests were performed on guinea-pig ileum and on mouse vas deferens according to Roselt et al., Acta Physiologica Scandinavia, 1975, 94, 142–144, and according to Nicolau et al., Arch. Int. Pharmacodyn., 1978, 236, 131–136.

The toxicity of the products according to the invention is compatible with their use as drugs. Thus they can be used for their psychotropic activity, especially for the treatment of thymus disorders, anxiety disorders, mood disorders, vomiting, memory disorders, cognitive disorders, neuropathy, migraine, stress, diseases of psychosomatic origin, epilepsy, dyskinesia or Parkinson's disease.

The compounds according to the invention can also be used as drugs for the treatment of appetite disorders, especially as anorexigenics, and for the treatment of schizophrenia, delusion disorders, psychotic disorders in general and disorders associated with the use of psychotic substances.

Furthermore, according to the invention, the compounds are useful as immunomodulators, in myorelaxation, asthma, epilepsy and glaucoma, in anticancer chemotherapy, in ischemia and angor, in orthostatic hypotension and in cardiac insufficiency.

The compounds according to the invention are generally administered in dosage units.

Said dosage units are preferably formulated in pharmaceutical compositions in which the active principle is mixed with at least one pharmaceutical excipient.

Thus, according to another of its features, the present invention relates to pharmaceutical compositions in which a compound of formula (I), one of its pharmaceutically acceptable salts or one of their solvates is present as the active principle.

The compounds of formula (I) above and their pharmaceutically acceptable salts can be used in daily doses of 0.01 to 100 mg per kilogram of body weight of the mammal to be treated, preferably in daily doses of 0.1 to 50 mg/kg. In humans, the dose can preferably vary from 0.5 to 4000 mg per day, more particularly from 2.5 to 1000 mg, depending on the age of the subject to be treated or the type of treatment, i.e. prophylactic or curative.

In the pharmaceutical compositions of the present invention for oral, sublingual, subcutaneous, intramuscular, intravenous, transdermal, local or rectal administration, the active principles can be administered to animals and humans in unit forms of administration, mixed with conventional pharmaceutical carriers. The appropriate unit forms of administration include forms for oral administration, such as tablets, gelatin capsules, powders, granules and solutions or suspensions to be taken orally, forms for sublingual and buccal administration, aerosols, implants, forms for subcutaneous, intramuscular, intravenous, intranasal or intraocular administration and forms for rectal administration.

In the pharmaceutical compositions of the present invention, the active principle is generally formulated in dosage units containing from 0.5 to 1000 mg, advantageously from 1 to 500 mg and preferably from 2 to 200 mg of said active principle per dosage unit for daily administrations.

If a solid composition in the form of tablets is prepared, the main active principle is mixed with a pharmaceutical vehicle such as silica, starch, lactose, magnesium stearate, talc or the like. The tablets can be coated with sucrose or other appropriate substances or else they can be treated so as to have a sustained or delayed activity and so as to release a predetermined amount of active principle continuously.

A preparation in the form of gelatin capsules is obtained by mixing the active principle with a diluent and incorporating the resulting mixture into soft or hard gelatin capsules.

A preparation in the form of a syrup or elixir can contain the active principle in conjunction with a sweetener, which is preferably calorie-free, methylparaben and propylparaben as antiseptics, a flavoring and an appropriate color.

The water-dispersible powders or granules can contain the active principle mixed with dispersants or wetting agents or with suspending agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral administration is effected using aqueous suspensions, isotonic saline solutions or injectable sterile solutions which contain pharmacologically compatible dispersants and/or wetting agents, for example propylene glycol or polyethylene glycol.

The active principle can also be formulated as microcapsules or microspheres, optionally with one or more carriers or additives.

The active principle can also be presented in the form of a complex with a cyclodextrin, for example α-, β- or γ-cyclodextrin, 2-hydroxypropyl-β-cyclodextrin or methyl-β-cyclodextrin.

The Examples which follow illustrate the invention without however implying a limitation.

The melting or decomposition points of the products, m.p., were measured in a capillary tube with a Tottoli apparatus.

The following abbreviations are used in the Preparations and in the Examples:

THF: tetrahydrofuran

Ether: diethyl ether

Iso ether: diisopropyl ether

EtOH: ethanol

AcOEt: ethyl acetate

Et: ethyl nPr: n-propyl

Ph: phenyl

Me: methyl

MeOH: methanol

DCM: dichloromethane

KOH: potassium hydroxide

AcOH: acetic acid

HCl: hydrochloric acid

NaCl: sodium chloride

RT: room temperature

M.p.: melting point

PREPARATIONS

Preparation 1.1

5-(4-Chlorophenyl)-1-(2,4-dichlorophenyl)-4-methylpyrazole-3-carboxylic Acid

A) Lithium salt of ethyl 4-(4-chlorophenyl)-3-methyl-4-oxido-2-oxobut-3-enoate 125 ml of a 1M solution of the lithium salt of hexamethyldisilazane in THF are added to 500 ml of ether under a nitrogen atmosphere. The mixture is cooled to −78° C. and a solution of 21 g of 4-chloropropiophenone in 100 ml of ether is added dropwise. After stirring for 45 minutes, 19.2 ml of ethyl oxalate are added rapidly and stirring is continued for 16 hours, the temperature being allowed to rise to RT. The precipitate formed is filtered off, washed with ether and dried under vacuum to give 12.6 g of the expected product.

B) Ethyl 5-(4-chlorophenyl)-1-(2,4-dichlorophenyl)-4-methylpyrazole-3-carboxylate 9.8 g of 2,4-dichlorophenylhydrazine are added to a solution of 12.6 g of the lithium salt obtained in the previous step in 70 ml of EtOH and the mixture is stirred for 16 hours at RT. The precipitate formed is filtered off, washed with EtOH and then with ether and dried under vacuum to give 12.6 g of a hydrazone, which is dissolved in 100 ml of AcOH. The solution is refluxed for 24 hours and the reaction mixture is then poured into 500 ml of iced water. It is extracted with AcOEt, washed with water and with a saturated solution of NaCl, dried over magnesium sulfate and evaporated under vacuum to give 9.6 g of the expected product after crystallization from iso ether. M.p.=124° C.

C) 5-(4-Chlorophenyl)-1-(2,4-dichlorophenyl)-4-methylpyrazole-3-carboxylic acid

A solution of 3.3 g of KOH in 70 ml of water is added to a solution of 9.6 g of the ester obtained in the previous step in 70 ml of MeOH and the reaction mixture is refluxed for 3 hours. It is poured into 200 ml of iced water and acidified to pH 1 by the addition of a 10% solution of HCl, and the precipitate formed is filtered off, washed with water and dried under vacuum to give 8.8 g of the expected acid. M.p.=211° C.

The esters and acids described in Table 1 below, which are useful for the synthesis of the derivatives described in Table 3, are prepared by following the procedure of Preparation 1 above.

TABLE 1

(II)

[Structure showing pyrazole with $CH_3$, $C(=O)OZ$, $g_4$-phenyl, $w_2$, $w_1$, $w_4$ substituents]

| Preparation | $w_2$ | $w_4$ | $g_4$ | Z = H M.p. °C. | Z = Et M.p. °C. |
|---|---|---|---|---|---|
| 1.2 | Cl | Cl | Me | 174 | 131 |
| 1.3 | Me | Cl | Me | 178 | 109 |
| 1.4 | Cl | Me | Me | 170 | |
| 1.5 | Me | Cl | Cl | 188 | 112 |
| 1.6 | Cl | Me | Cl | 206 | |

Preparation 1.7

5-(4-Chlorophenyl)-1-(2,4-dichlorophenyl)pyrazole-3-carboxylic Acid

A) Sodium salt of methyl 4-(4-chlorophenyl)-4-oxido-2-oxobut-3-enoate 12 g of sodium are dissolved in 250 ml of anhydrous methanol. A mixture of 64.6 ml of 4-chloroacetophenone and 67.1 ml of diethyl oxalate in 600 ml of methanol is then added, the temperature being kept below 10° C. The reaction mixture is then stirred at room temperature for 3 hours, after which 1 l of dry ether is added. Stirring is continued for 20 minutes and the precipitate is filtered off, washed with ether and dried under vacuum to give 74.6 g of the expected sodium salt.

B) Methyl 5-(4-chlorophenyl)-1-(2,4-dichlorophenyl)pyrazole-3-carboxylate

A suspension of 26.3 g of the sodium salt obtained above and 23.5 g of 2,4-dichlorophenylhydrazine hydrochloride in 250 ml of acetic acid is refluxed for 4 hours. After cooling, the mixture is poured onto 250 g of ice and the crystals obtained are filtered off, washed with water and dried under vacuum to give 26.3 g of the ester. M.p.=167° C.

C) 5-(4-Chlorophenyl)-1-(2,4-dichlorophenyl)pyrazole-3-carboxylic acid

A solution of 3.70 g of KOH in 35 ml of water is added to a solution of 10.0 g of the ester obtained above in 35 ml of methanol. The mixture is refluxed for 4 hours, cooled to room temperature, poured into 100 ml of water and then neutralized with a 5% solution of HCl. The crystals obtained are filtered off, washed with water and then with pentane and dried under vacuum to give 9.50 g of the acid. M.p.=185° C.

The acids described in Table 2 below are prepared by following the procedure of Preparation 1.7 above.

TABLE 2

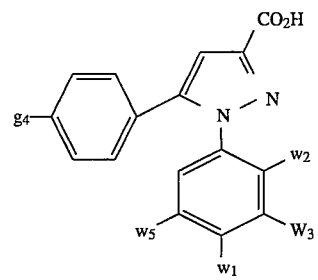

| Preparation | $w_2$ | $w_3$ | $w_4$ | $w_5$ | $g_4$ | M.p. °C. |
|---|---|---|---|---|---|---|
| 1.8 | H | Cl | I | H | Me | 140 |
| 1.9 | H | Me | H | Me | Me | 239 |
| 1.10 | Me | H | Cl | H | Me | 134 |
| 1.11 | Me | H | Me | H | Me | 189 |
| 1.12 | Me | H | H | Me | Me | 206 |
| 1.13 | H | Cl | Me | H | Me | 161 |
| 1.14 | H | Me | Me | H | Me | 199 |
| 1.15 | Cl | Cl | Cl | H | Me | 235 |
| 1.16 | H | Me | Me | H | Cl | 189 |
| 1.17 | Me | H | H | Me | Cl | 206 |
| 1.18 | H | Cl | Me | H | Cl | 143 |

Preparation 1.19

5-(4-Chlorophenyl)-1-(2,4-dichlorophenyl)-4-ethylpyrazole-3-carboxylic Acid

A) Ethyl 5-(4-chlorophenyl)-1-(2,4-dichlorophenyl)-4-bromomethylpyrazole-3-carboxylate 0.70 g of N-bromosuccinimide and a spatula tip of benzoyl peroxide are added to a solution of 1.62 g of the ethyl 5-(4-chlorophenyl)-1-(2,4-dichlorophenyl)-4-methylpyrazole-3-carboxylate described in Preparation 1.1, step B, in 20 ml of $CCl_4$. The mixture is refluxed for 16 hours, the white precipitate is then filtered off and the filtrate is washed with water and then with a saturated solution of NaCl to give 2.20 g of a yellow foam, which is crystallized from iso ether to give 1.00 g of white crystals. M.p.=108° C.

B) Ethyl 5-(4-chlorophenyl)-1-(2,4-dichlorophenyl)-4-ethylpyrazole-3-carboxylate 2.97 ml of a 1.6M solution of methyllithium in ether are added dropwise to a suspension of 0.34 g of cuprous bromide in 20 ml of ethyl ether, cooled to −20° C. under nitrogen. The mixture is stirred for 15 minutes at −20° C. and then cooled to −40° C. and a solution of 1.00 g of the ester obtained in the previous step in 20 ml of ether is added dropwise. The temperature is slowly allowed to return to RT and the mixture is stirred for a further 3 hours before being hydroyzed with 50 ml of a saturated solution of $NH_4Cl$. The mixture is extracted with ether and washed with water and then with a saturated solution of NaCl to give 0.82 g of a pale green solid, which is chromatographed on a silica column using AcOEt/hexane (15/85; v/v) as the eluent to give 0.35 g of white crystals. M.p.=105° C.

C) 5-(4-Chlorophenyl)-1-(2,4-dichlorophenyl)-4-ethylpyrazole-3-carboxylic acid

A solution of 0.78 g of potassium hydroxide in 20 ml of water is added to a solution of 2.35 g of the ester obtained in the previous step in 20 ml of methanol and the mixture is refluxed for 3 hours. It is poured into 100 ml of iced water and then acidified to pH 1 by the addition of 10% HCl. The white solid obtained is filtered off, washed with water and dried under vacuum to give 2.58 g of the expected acid. M.p.=215° C.

Preparation 1.20

5-(4-Chlorophenyl)-1-($_{2,4}$-dichlorophenyl)-4-pentylpyrazole-3-carboxylic Acid 13.2 ml of a 1.6M solution of butyllithium in hexane are added dropwise to a suspension of 2.04 g of cuprous iodide in 20 ml of ethyl ether, cooled to −40° C. under nitrogen. The mixture is cooled to −70° C. and a solution of 1.50 g of methyl 5-(4-chlorophenyl)-1-(2,4-dichlorophenyl)-4-bromomethylpyrazole-3-carboxylate, obtained as in Preparation 1.19, in 20 ml of ether is added dropwise. The temperature is slowly allowed to return to RT and the mixture is stirred for 3 hours before being hydrolyzed with 50 ml of a saturated solution of $NH_4Cl$. The mixture is extracted with ether and washed with water and then with a saturated solution of NaCl. After drying over $MgSO_4$ and evaporation of the solvents, 1.37 g of a viscous oil are obtained which is chromatographed on a silica column using AcOEt/hexane (10/90; v/v) as the eluent to give 0.42 g of a viscous oil (mixture of methyl and butyl esters). A solution of 0.24 g of potassium hydroxide in 15 ml of water is added to a solution of 0.42 g of the above product in 15 ml of methanol and the mixture is refluxed for 3 hours. It is poured into 100 ml of iced water and then acidified to pH 1 by the addition of 10% HCl. The white solid is filtered off, washed with water and dried under vacuum to give 0.39 g of the expected acid. M.p.=187° C.

Preparation 2.1

1-Amino-1,2,3,6-tetrahydropyridine Hydrochloride

A) 1-Nitroso-1,2,3,6-tetrahydropyridine

A solution of 2.0 ml of 1,2,3,6-tetrahydropyridine in 6 ml of water is cooled to 0° C., 16 ml of AcOH are added and a solution of 9.1 g of sodium nitrite in 20 ml of water is then added dropwise. The mixture is stirred for 16 hours at RT and then extracted with DCM, washed with a saturated solution of sodium hydrogencarbonate and with a saturated solution of sodium chloride and dried over magnesium sulfate and the solvent is evaporated off under vacuum to give 2.34 g of a yellow oil, which is used as such in the next step.

B) 1-Amino-1,2,3,6-tetrahydropyridine hydrochloride

A solution of 2.34 g of the compound obtained in the previous step in 80 ml of ether is cooled to 0° C. and a suspension of 2.38 g of lithium aluminum hydride in 60 ml of ether is added dropwise. The reaction mixture is refluxed for 3 hours and then cooled to 0° C. and 2.3 ml of water, then 2.3 ml of a 15% aqueous solution of NaOH and finally 6.9 ml of water are added. The precipitate formed is filtered off and washed with ether, the filtrate is then taken up with ether, washed with a saturated solution of sodium chloride and dried over magnesium sulfate and the solvent is evaporated off under vacuum. The oil obtained is dissolved in 15 ml of ether, and a saturated solution of gaseous HCl in ether is added dropwise to pH 1. The white precipitate formed is filtered off, washed with ether and dried under vacuum to give 1.84 g of the expected hydrochloride. M.p.=142° C.

Note: The $LiAlH_4$ reduction step may have a rather long initiation time and then start rapidly and very exothermically.

Preparations 2.2 to 2.14

1-Amino-4-phenylpiperidine (m.p.=65° C.), 1-amino-3-azabicyclo(3.2.2)nonane hydrochloride (m.p.=210° C.), cis- and trans-1-amino-3,5-dimethylpiperidines (liquid), 1-amino-3,3-dimethylpiperidine (liquid), 1-amino-4-methoxypiperidine (m.p.=147° C.), 1-amino-8-azabicyclo(4.3.0)non-3-ene hydrochloride (m.p.=84° C.), 1-amino-8-azaspiro(4.5)decane hydrochloride (m.p.=102° C.), 2-amino-2-azaadamantane (m.p.=90° C.), cyclohexylhydrazine (liquid) and 1-methyl-1-cyclohexylhydrazine (liquid) are prepared starting from the corresponding amines by the procedure described in steps A and B of Preparation 2.1. 1,1-diethylhydrazine and 1,1-dipropyl-hydrazine are prepared from the corresponding nitrosamines by the procedure described in step B of Preparation 2.1.

Preparation 2.15

1-Ethylamino-1,2,3,6-tetrahydropyridine

A) 1-Methyleneimino-1,2,3,6-tetrahydropyridine 100 ml of a 37% aqueous solution of formaldehyde are added dropwise to 22 g of 1-amino-1,2,3,6-tetrahydropyridine (Preparation 2.1) and the mixture is then stirred at RT for 3 hours. It is saturated with solid NaOH at 0° C. and then extracted with ether. The ether phase is dried over $MgSO_4$ and the solvents are evaporated off. 6.5 g of the expected product are collected by vacuum distillation (b.p.=50°–55° C. under 20 mm Hg).

B) 1-Ethylamino-1,2,3,6-tetrahydropyridine

A solution of 3.25 g of 1-methyleneimino-1,2,3,6-tetrahydropyridine, obtained in the previous step, in 25 ml of toluene is added dropwise to 14 ml of a 3M solution of methylmagnesium bromide in THF, the mixture being heated to 60° C. When the addition has ended, the mixture is refluxed for 2 hours and then cooled and poured onto 35 g of ice to which 6.7 ml of concentrated HCl have been added. The mixture is concentrated under vacuum and 11 ml of 30% NaOH are added dropwise at 0° C. to the residue obtained. The mixture is extracted with ether and the organic phase is dried over $MgSO_4$ and evaporated under vacuum to give 2.80 g of the expected product (oil).

NMR at 200 MHz in DMSO 1 ppm:t:3H 2.11–2.22 ppm:m:2H 2.67–2.80 ppm:m:4H 3.13 ppm:s:2H 5.59–5.73 ppm:m:2H Preparation 2.16

1-Methylamino-1,2,3,6-tetrahydropyridine Hydrochloride

A solution of 2 g of 1-methyleneimino-1,2,3,6-tetrahydropyridine, obtained in Preparation 2.14, step A, in 10 ml of ether is added dropwise to a solution of 0.38 g of $LiAlH_4$ in 15 ml of ether, cooled to 0° C., and the mixture is then refluxed for 12 hours. It is hydrolyzed at 0° C. by the successive addition of 0.38 ml of water, 0.38 ml of 15%

NaOH and 1.13 ml of water. The mixture is filtered and the filtrate is evaporated under vacuum and then dissolved in 10 ml of acetone. A saturated solution of HCl in ether is added dropwise to acid pH and the oil obtained is then decanted and dried under vacuum to give 2.10 g of a white solid. M.p.=107° C.

EXAMPLE 1

N-(1,2,3,6-Tetrahydropyridin-1-yl)-5-(4-chlorophenyl)-1-(2,4-dichlorophenyl)-4-methylpyrazole-3-carboxamide Hydrochloride A) 5-(4-Chlorophenyl)-1-(2,4-dichlorophenyl)-4-methylpyrazole-3-carboxylic acid chloride 5 ml of thionyl chloride are added to a suspension of 8.8 g of the acid obtained in Preparation 1.1 in 90 ml of toluene and the reaction mixture is refluxed for 3 hours. It is evaporated to dryness under vacuum, the residue is taken up with 90 ml of toluene and the mixture is evaporated under vacuum again to give 8 g of the expected acid chloride, which is used as such in the next step.

B) N-(1,2,3,6-Tetrahydropyridin-1-yl)-5-(4-chlorophenyl)-1-(2,4-dichlorophenyl)-4-methylpyrazole-3-carboxamide hydrochloride A solution of 0.59 g of 1-amino-1,2,3,6-tetrahydropyridine hydrochloride (obtained in Preparation 2.1) and 1.45 ml of triethylamine in 20 ml of DCM is cooled to 0° C. and a solution of 1.32 g of 5-(4-chlorophenyl)-1-(2,4-dichlorophenyl)-4-methylpyrazole-3-carboxylic acid chloride, obtained in the previous step, in 20 ml of DCM is added dropwise. The mixture is stirred for 3 hours, the temperature being allowed to rise to RT, and is then poured into 100 ml of iced water. It is extracted with DCM, washed with water and then with a saturated solution of NaCl and dried over magnesium sulfate and the solvent is evaporated off under vacuum. The residue is chromatographed on silica using a toluene/AcOEt mixture (90/10; v/v) as the eluent to give 1.0 g of a colorless foam, which is dissolved in 15 ml of ether; a saturated solution of gaseous HCl in ether is added dropwise to pH 1. The white precipitate formed is filtered off, washed with ether and dried under vacuum to give 0.55 g of the expected hydrochloride. M.p.=200° C. (decomposition).

The products described in Table 3 below are prepared by following the procedure of Example 1.

TABLE 3

[Structure: pyrazole core with 4-CH₃, 3-C(O)NH-N(R₅)(R₆), 5-(4-g₄-phenyl), 1-(2-w₂,4-w₄-phenyl)]

| Example | $w_2$ | $w_4$ | $g_4$ | $-N(R_5)(R_6)$ | M.p. °C. | Salt |
|---|---|---|---|---|---|---|
| 2 | Cl | Cl | Cl | 2,6-dimethylpiperidin-1-yl | 154 | HCl |
| 3 | Cl | Cl | Cl | 4-phenylpiperidin-1-yl | 156 | HCl |
| 4 | Cl | Cl | Cl | 2-azabicyclo group | 144 | HCl |
| 5 | Cl | Cl | Cl | 3,5-dimethylpiperidin-1-yl | 184 | HCl less polar isomer |
| 6 | Cl | Cl | Cl | 3,5-dimethylpiperidin-1-yl | 172 | HCl more polar isomer |
| 7 | Cl | Cl | Cl | 4,4-dimethylpiperidin-1-yl | 195 | HCl |
| 8 | Cl | Cl | Cl | 4-methoxypiperidin-1-yl | 147 | |
| 9 | Cl | Cl | Cl | spiro[piperidine-cyclopentane] | 216 | HCl |

TABLE 3-continued

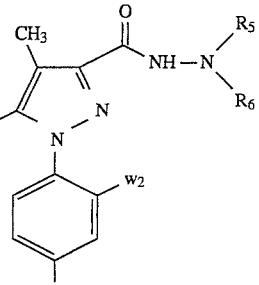

| Example | w2 | w4 | g4 | —N(R5)(R6) | M.p. °C. | Salt |
|---|---|---|---|---|---|---|
| 10 | Cl | Cl | Cl | 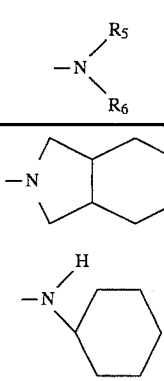 | 144 | HCl |
| 11 | Cl | Cl | Cl | 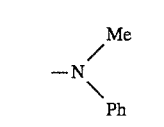 | 147 | HCl |
| 12 | Cl | Cl | Cl | 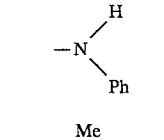 | 163 | |
| 13 | Cl | Cl | Cl | 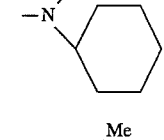 | 102 | |
| 14 | Cl | Cl | Cl | 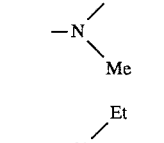 | 138 | HCl |
| 15 | Cl | Cl | Cl | 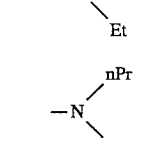 | 214 | HCl |
| 16 | Cl | Cl | Cl | 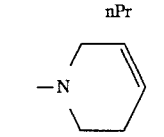 | 216 | HCl |
| 17 | Cl | Cl | Cl | 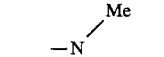 | 167 | HCl |
| 18 | Cl | Cl | Me |  | 187 | HCl |
| 19 | Cl | Cl | Me | 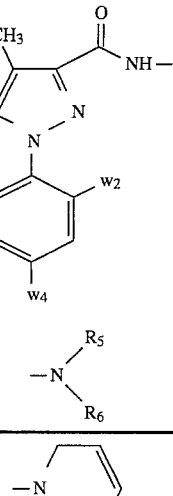 | 210 | HCl |
| 20 | Me | Cl | Me | 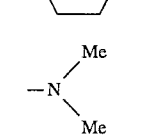 | 167 | HCl |
| 21 | Me | Cl | Me | 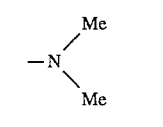 | 213 | HCl |
| 22 | Cl | Me | Me | 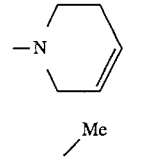 | 208 | HCl |
| 23 | Me | Cl | Cl | 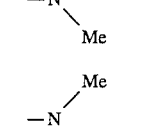 | 189 | HCl |
| 24 | Me | Cl | Cl | 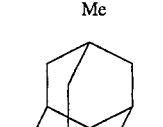 | 213 | HCl |
| 25 | Cl | Me | Cl | | 212 | HCl |
| 26 | Cl | Cl | Cl | 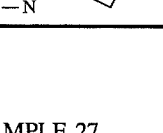 | 235 | |

EXAMPLE 27

N-Ethyl-N-(1,2,3,6-tetrahydropyridin-1-yl)-5-(4-chlorophenyl)-1-(2,4-dichlorophenyl)-4-methylpyrazole-3-carboxamide Prepared according to Example 1 starting from 1-ethylamino-1,2,3,6-tetrahydropyridine (Preparation 2.15) instead of 1-amino-1,2,3,6-tetrahydropyridine hydrochloride. M.p.=109° C.

EXAMPLE 28

N-Methyl-N-(1,2,3,6-tetrahydropyridin-1-yl)-5-(4-chlorophenyl)-1-(2,4-dichlorophenyl)-4-methylpyrazole-3-carboxamide Prepared according to Example 1 starting from 1-methylamino-1,2,3,6-tetrahydropyridine (Preparation 2.16) instead of 1-amino-1,2,3,6-tetrahydropyridine hydrochloride. M.p.=138° C.

EXAMPLE 29

N-(2,6-Dimethylpiperidin-1-yl)-5-(4-chlorophenyl)-1-(2,4-dichlorophenyl)pyrazole-3-carboxamide Hydrochloride A) 5-(4-Chlorophenyl)-1-(2,4-dichlorophenyl)pyrazole-3-carboxylic acid chloride 5.8 ml of thionyl chloride are added to a suspension of 9.50 g of the acid obtained in Preparation 1.7 in 100 ml of toluene and the reaction mixture is refluxed for 3 hours. It is evaporated to dryness under vacuum, the residue is taken up with 50 ml of toluene and the solvent is evaporated off under vacuum to give 8.28 g of the expected acid chloride, which is used as such in the next step.

B) N-(2,6-Dimethylpiperidin-1-yl)-5-(4-chlorophenyl)-1-(2,4-dichlorophenyl)pyrazole-3-carboxamide hydrochloride This compound is prepared by the procedure described in EXAMPLE 1 starting from 1-amino-2,6-dimethylpiperidine and 5-(4-chlorophenyl)-1-(2,4-dichlorophenyl)pyrazole-3-carboxylic acid chloride. M.p.=195° C.

EXAMPLE 30

1-Methyl-1-[5-(4-chlorophenyl)-1-(2,4-dichlorophenyl)-4-methylpyrazole-3-carboxamido]piperidinium Iodide and 1-Methyl-1-[5-(4-chlorophenyl)-1-(2,4-dichlorophenyl)-4-methylpyrazole-3-carboxamido]piperidinium Chloride A) N-(Piperidin-1-yl)-5-(4-dichlorophenyl)-1-(2,4-dichlorophenyl)-4-methylpyrazole-3-carboxamide This compound is prepared by the procedure described in EXAMPLE 1 starting from 1-aminopiperidine and 5-(4-chlorophenyl)-1-(2,4-dichlorophenyl)-4-methylpyrazole-3-carboxylic acid chloride. M.p.=148° C.

B) 1-Methyl-1-[5-(4-chlorophenyl)-1-(2,4-dichlorophenyl)-4-methylpyrazole-3-carboxamido]piperidinium iodide 0.35 g of methyl iodide is added to a solution of 0.23 g of the compound obtained in the previous step in 5 ml of acetone and the mixture is refluxed for 24 hours. The solvent is evaporated off under vacuum and the residue is taken up with ether. The precipitate formed is filtered off, washed with ether and dried under vacuum to give 0.16 g of the expected iodide. M.p.=136° C. (decomposition).

C) 1-Methyl-1-[5-(4-chlorophenyl)-1-(2,4-dichlorophenyl)-4-methylpyrazole-3-carboxamido]piperidinium chloride A solution of 0.50 g of the amide obtained in step A in 3.00 g of methyl iodide is stirred at RT for 72 hours. The solvent is evaporated off under vacuum and the residue is taken up with an MeOH/H$_2$O mixture (10/90; v/v) and eluted with the same mixture on a column of Amberlite IRA400.HCl resin. The product obtained is crystallized from an ether/iso ether mixture to give 0.26 g of a white solid. M.p.=210° C.

EXAMPLE 31

N-[5-(4-Chlorophenyl)-1-(2,4-dichlorophenyl)-4-methylpyrazole-3-carboxamido]quinuclidinium Mesitylenesulfonate 3 ml of a 1M solution of sodium ethylate in ethanol are evaporated to dryness under vacuum and the white residue obtained is taken up with 7 ml of anhydrous THF. 1.00 g of 1-aminoquinuclidinium mesitylenesulfonate (prepared according to J. Heterocycl. Chem., 1980, 17, 1241) is added to this solution, the mixture is stirred for 2 hours at RT, 1.2 g of the ester described in Preparation 1.1, step B, are then added and the mixture is stirred at RT for 5 days. The residual solid is filtered off, the mother liquors are evaporated and the residue is taken up with 15 ml of DCM. This solution is washed with a 0.1N solution of HCl and then with a saturated solution of NaCl. After drying over MgSO$_4$ and evaporation under vacuum, a white solid is obtained which is recrystallized from an iso ether/acetone mixture (90/10; v/v) to give 70 mg of a crystalline solid. M.p.=154° C.

EXAMPLE 32

N-(1,2,3,6-Tetrahydropyridin-1-yl)-5-(4-chlorophenyl)-1-(2,4-dichlorophenyl)-4-ethylpyrazole-3-carboxamide Hydrochloride A) 5-(4-Chlorophenyl)-1-(2,4-dichlorophenyl)-4-ethylpyrazole-3-carboxylic acid chloride 1.43 ml of thionyl chloride are added to a suspension of 2.58 g of the acid obtained in Preparation 1.19 in 20 ml of toluene and the reaction mixture is refluxed for 3 hours. It is evaporated to dryness under vacuum and the residue is taken up with 20 ml of toluene, which is evaporated off under vacuum (twice in succession) to give 2.28 g of the expected acid chloride.

B) N-(1,2,3,6-Tetrahydropyridin-1-yl)-5-(4-chlorophenyl)-1-(2,4-dichlorophenyl)-4-ethylpyrazole-3-carboxamide hydrochloride A solution of 0.61 g of the above acid chloride in 10 ml of DCM is added dropwise to a solution of 0.21 g of 1-amino-1,2,3,6-tetrahydropyridine hydrochloride and 0.43 ml of triethylamine in 10 ml of DCM, cooled to 0° C. The reaction mixture is stirred at RT for 3 hours and is then poured into 100 ml of iced water. The organic phase is extracted with DCM, washed with water and then with a saturated solution of NaCl and dried over MgSO$_4$. Evaporation of the solvents gives a crude product, which is purified by crystallization from iso ether to give 0.35 g of the expected carboxamide. A solution of gaseous HCl in ether is added dropwise to a solution of 0.35 g of this carboxamide in 10 ml of ether until the pH is acid. The white precipitate formed is filtered off, washed with ether and dried under vacuum to give 0.27 g of the expected hydrochloride. M.p.=205° C. (decomposition).

EXAMPLE 33

N-(1,2,3,6-Tetrahydropyridin-1-yl)-5-(4-chlorophenyl)-1-(2,4-dichlorophenyl)-4-pentylpyrazole-3-carboxamide A) 5-(4-Chlorophenyl)-1-(2,4-dichlorophenyl)-4-pentylpyrazole-3-carboxylic acid chloride 0.50 ml of thionyl chloride is added to a suspension of 0.39 g of the acid obtained in Preparation 1.20 in 8 ml of toluene and the reaction mixture is refluxed for 3 hours. It is evaporated to dryness under vacuum and the residue is taken up with 20 ml of toluene, which is evaporated off again under vacuum (twice in succession) to give 0.44 g of the expected acid chloride.

B) N-(1,2,3,6-Tetrahydropyridin-1-yl)-5-(4-chlorophenyl)-1-(2,4-dichlorophenyl)-4-pentylpyrazole-3-carboxamide A solution of 0.22 g of the above acid chloride in 8 ml of DCM is added dropwise to a solution of 0.061 g of 1-amino-1,2,3,6-tetrahydropyridine and 0.079 ml of triethylamine in 10 ml of DCM, cooled to 0° C. The reaction mixture is stirred at RT for 16 hours and is then poured into 100 ml of iced water. The organic phase is extracted with DCM, washed with water and then with a saturated solution of-NaCl and dried over $MgSO_4$. Evaporation of the solvents gives a crude product, which is purified by chromatography on a silica column using AcOEt/toluene (8/92; v/v) as the eluent, followed by crystallization from iso ether, to give 0.12 g of the expected product. M.p.=150° C.

What is claimed is:

1. A compound of the formula

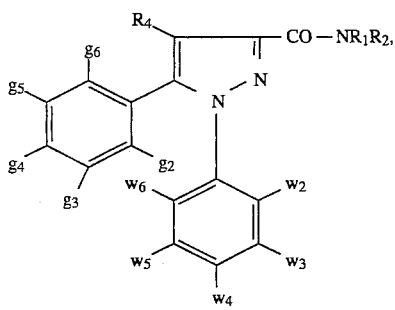

(I)

in which:

$g_2$, $g_3$, $g_4$, $g_5$ and $g_6$, and $w_2$, $w_3$, $w_4$, $w_5$ and $w_6$, are identical or different and are independently hydrogen, a chlorine, bromine or iodine atom, a $(C_1-C_3)$alkyl, a $(C_1-C_3)$alkoxy, a trifluoromethyl or a nitro group and $g_4$ can also be a phenyl group;

$R_1$ is a $(C_1-C_6)$alkyl or a hydrogen;

$R_2$ is $-^+NR_3R_5R_6$ or $-NR_5R_6$;

$R_3$ is a $(C_1-C_6)$alkyl or $R_3$ forms a bridge with one of the atoms of the heterocyclic radical formed by $NR_5R_6$;

$R_4$ is hydrogen or a $(C_1-C_5)$alkyl; and $R_5$ is hydrogen or a $(C_1-C_6)$alkyl and $R_6$ is hydrogen, a $(C_1-C_6)$alkyl, a phenyl or a $(C_3-C_8)$cycloalkyl, with the proviso that both $R_5$ and $R_6$ cannot both be H; or $R_5$ and $R_6$, together with the nitrogen atom to which they are bonded, form a 5- to 10-membered saturated or unsaturated heterocyclic radical which is unsubstituted or monosubstituted or polysubstituted by a $(C_1-C_6)$alkyl, a benzyl, a phenyl, a hydroxyl, a $(C_1-C_6)$alkoxy or a halogen, with the proviso that if $R_2$ is $NR_5R_6$, $R_5$ and $R_6$, together with the nitrogen atom to which they are bonded, form a heterocyclic radical other than a 5- to 8-membered saturated radical which is unsubstituted or substituted by a $(C_1-C_3)$alkyl, a hydroxyl or a benzyl, its salts and their solvates.

2. A compound according to claim 1 in which at least one of the substituents $w_2$, $w_3$, $w_4$, $w_5$, $w_6$, $g_2$, $g_3$, $g_4$, $g_5$ and $g_6$ is other than hydrogen.

3. A compound according to claim 1 in which at least one of the substituents $w_2$, $w_3$, $w_4$, $w_5$, $w_6$, $g_2$, $g_3$, $g_4$, $g_5$ and $g_6$ is selected from a chlorine and a methyl.

4. A compound according to claim 1 in which $w_2$, $w_4$ and $g_4$ are chlorine atoms.

5. A compound according to claim 1 in which $R_4$ is H, methyl or ethyl.

6. A compound according to claim 1 in which $w_2$, $w_4$ and $g_4$ are each a chlorine, $R_1$ is hydrogen, $R_4$ is a methyl or an ethyl and $R_2$ is as defined for (I) in claim 1.

7. A compound according to claim 1 in which $g_4$ is a chlorine or a methyl, $w_3$ and $w_4$, or $w_2$ and $w_5$, are selected from chlorine and methyl, $R_1$ is a methyl, an ethyl or a propyl, $R_4$ is hydrogen and $R_2$ is as defined for (I) in claim 1.

8. A compound according to claim 1 in which $R_2$ is a 5-, 6- or 7-membered monounsaturated heterocyclic radical.

9. A compound according to claim 8 in which $R_2$ is a 1,2,3,6-tetrahydropyridin-1-yl group.

10. A pharmaceutical composition which contains an effective amount of a compound according to claim 1, or one of its pharmaceutically acceptable salts, mixed with at least one pharmaceutically acceptable excipient.

11. A pharmaceutical composition according to claim 10, which is in the form of a dosage unit.

12. A pharmaceutical composition according to claim 11 which contains from 0.5 to 1000 mg of active principle.

13. A compound according to claim 2 in which at least one of the substituents $w_2$, $w_3$, $w_4$, $w_5$, $w_6$, $g_2$, $g_3$, $g_4$, $g_5$ and $g_6$ is a chlorine atom or a methyl group.

14. A compound according to claim 2 in which $w_2$, $w_4$ and $g_4$ are chlorine atoms.

15. A compound according to claim 2 in which $R_4$ is hydrogen, methyl or ethyl.

16. A compound according to claim 2 in which $R_3$ is a 5-, 6- or 7-membered monounsaturated heterocycle.

17. A pharmaceutical composition which contains an effective amount of a compound according to claim 2, or one of its pharmaceutically acceptable salts, mixed with at least one pharmaceutically acceptable substituent.

18. A compound according to claim 1 which is N-(1,2,3,6-tetrahydropyridin-1-yl)-5-(4-chlorophenyl)-1-(2,1-dichlorophenyl)-4-ethylpyrazole-3-carboxamide hydrochloride.

19. A compound according to claim 1 which is N-(1,2,3,6-tetrahydropyridin-1-yl)-5-(4-chlorophenyl)-1-(2,4-dichlorophenyl) 4-methylpyrazole-3-carboxamide hydrochloride.

20. A compound according to claim 1 which is N-[8-azabicyclo[4.3.0]non-3-en-8-yl]-5-(4-chlorophenyl)-1-(2,4-dichlorophenyl)-4-methylpyrazole-3-carboxamide hydrochloride.

* * * * *

UNITED STATES PATENT AND TRADEMARK OFFICE
CERTIFICATE OF CORRECTION

PATENT NO. : 5,462,960
DATED : October 31, 1995
INVENTOR(S) : Francis BARTH et al.

It is certified that error appears in the above-indentified patent and that said Letters Patent is hereby corrected as shown below:

Column 6, Scheme 1 (in Formula (III)), delete "(Alk=CH $C_2H_5$)"

and insert --(ALK=$CH_3,C_2H_5$)--;

Column 12, Table 2 in the formula (for the substituent of position 4- of the phenyl ring), delete "$w_1$" and insert --$w_4$--;

Column 12, line 66, delete "hydroyzed" and insert --hydrolyzed--; and

Column 14, line 63, delete "Preparation 2.14" and insert --Preparation 2.15--.

Claim 16, line 1 (Column 22, line 41), delete "$R_3$" and insert --$R_2$--; and

UNITED STATES PATENT AND TRADEMARK OFFICE
CERTIFICATE OF CORRECTION

PATENT NO. : 5,462,960

DATED : October 31, 1995

INVENTOR(S) : Francis BARTH et al.

It is certified that error appears in the above-indentified patent and that said Letters Patent is hereby corrected as shown below:

Claim 18, line 2 (Column 22, line 48), delete "-1-(2,1-" and insert ---1-(2,4---.

Signed and Sealed this

Twenty-fourth Day of December, 1996

Attest:

BRUCE LEHMAN

*Attesting Officer*  *Commissioner of Patents and Trademarks*